US010143467B2

(12) United States Patent
Altman et al.

(10) Patent No.: US 10,143,467 B2
(45) Date of Patent: Dec. 4, 2018

(54) SUTURING ASSEMBLY WITH SPACER

(71) Applicant: EasyLap Ltd., Kfar Truman (IL)

(72) Inventors: Nir Altman, Kfar Etzion (IL); Izhak Fabian, Kfar Truman (IL)

(73) Assignee: THD Lap Ltd., Kfar Truman (IL)

( * ) Notice: Subject to any disclaimer, the term of this patent is extended or adjusted under 35 U.S.C. 154(b) by 791 days.

(21) Appl. No.: 14/356,632

(22) PCT Filed: Nov. 8, 2012

(86) PCT No.: PCT/US2012/064053
§ 371 (c)(1),
(2) Date: May 7, 2014

(87) PCT Pub. No.: WO2013/070841
PCT Pub. Date: May 16, 2013

(65) Prior Publication Data
US 2014/0371791 A1 Dec. 18, 2014

Related U.S. Application Data

(60) Provisional application No. 61/557,482, filed on Nov. 9, 2011.

(51) Int. Cl.
*A61B 17/04* (2006.01)
*A61B 17/06* (2006.01)

(52) U.S. Cl.
CPC .... *A61B 17/06061* (2013.01); *A61B 17/0482* (2013.01); *A61B 17/0483* (2013.01); *A61B 17/0485* (2013.01)

(58) Field of Classification Search
CPC . A61B 17/04; A61B 17/0466–17/0469; A61B 17/0482; A61B 17/0485; A61B 2017/0472
See application file for complete search history.

(56) References Cited

U.S. PATENT DOCUMENTS

2003/0004544 A1   1/2003   Kawashima
2006/0069398 A1*  3/2006   Suzuki ............... A61B 17/0482
                                                       606/148
2009/0264905 A1  10/2009   Funada

FOREIGN PATENT DOCUMENTS

| EP | 1598017 | 11/2005 |
| EP | 2005892 | 12/2008 |
| WO | 95/33408 | 12/1995 |
| WO | 2007/073931 | 7/2007 |

OTHER PUBLICATIONS

PCT Written Opinion PCT/US2012/064053, dated Mar. 22, 2013.

* cited by examiner

*Primary Examiner* — Darwin Erezo
*Assistant Examiner* — Jonathan Hollm
(74) *Attorney, Agent, or Firm* — Dekel Patent Ltd.; David Klein

(57) ABSTRACT

A suturing assembly including a first puncture element including a sharp distal end for puncturing tissue, a second puncture element including a sharp distal end for puncturing tissue, the distal ends of the first and second puncture elements being spaced from each other by a gap, and a spacer arranged for sliding distally and proximally on at least one of the first and second puncture elements.

9 Claims, 7 Drawing Sheets

SUTURING ASSEMBLY WITH SPACER

FIELD OF THE INVENTION

The present invention relates generally to suturing devices and methods, such as for the percutaneous closure of body lumens and tissues by means of sutures.

BACKGROUND OF THE INVENTION

Many suturing devices are known in the art that puncture the skin with needles and percutaneously deliver sutures to the site. For example, PCT Patent Application WO 2009069119 discloses a suturing assembly 10, which is briefly described here with reference to FIGS. 1 and 2.

Suturing assembly 10 includes a first puncture element 12 including a sharp distal end 14 for puncturing tissue, and a second puncture element 16 including a sharp distal end 18 for puncturing tissue. The distal ends 14 and 18 of first and second puncture elements 12 and 14 are spaced from each other by a gap 20. Preferably, but not necessarily, first and second puncture elements 12 and 14 are parallel to each other.

First and second puncture elements 12 and 16 are hollow. A suture manipulating assembly 22 that includes a suture thread receiving member 24 and a suture grabber 26, which can be passed into the hollow portions of first and second puncture elements 12 and 16, respectively. First and second puncture elements 12 and 16 are provided with distal funnel cups 28 and 30, respectively, for guiding insertion of suture thread receiving member 24 and suture grabber 26. The funnel cups 28 and 30 also serve as stops to limit movement of suture thread receiving member 24 and suture grabber 26 into first and second puncture elements 12 and 16. Proximal ends of suture thread receiving member 24 and suture grabber 26 are mounted on a handle assembly 32. Suture thread receiving member 24 is mounted on an adjustable block 17 of handle assembly 32. Adjustable block 17 is arranged for moving with respect to a distal block 19 of handle assembly 32.

Suture thread 38 is placed over a distal end of suture thread receiving member 24. As seen in FIG. 2, the suture grabber 26 is arranged to grab suture thread 38 at the distal end 14 of first puncture element 12 and pull suture thread 38 over the gap to second puncture element 16.

Briefly, in operation of suturing assembly 10, first and second puncture elements 12 and 16 are first pushed into tissue and the sharp distal ends 14 and 18 puncture a tissue wall. The suture thread receiving member 24 and suture grabber 26 are introduced into the hollow portions of first and second puncture elements 12 and 16, respectively. When the suture thread receiving member 24 is pushed fully up to funnel cup 28, the suture thread 38 passes from a near side of the tissue wall to a far side of the tissue wall. When suture grabber 26 is pushed fully up to funnel cup 30, suture grabber 30 swings out of second puncture element 16 towards the suture thread 38 at the distal end 14 of first puncture element 12. Suture thread 38 is now caught and grabbed by suture grabber 26, as seen in FIG. 2. The suture thread receiving member 24 and suture grabber 26 are then pulled proximally (backwards). This movement pulls suture grabber 26 back into second puncture element 16. As suture grabber 26 moves proximally it brings along with it suture thread 38 over the gap 20, proximally away from the distal end 18 of second puncture element 16, and back through to the near side of the tissue wall. Afterwards, the suture thread 38 may be secured to form a stitch.

SUMMARY OF THE INVENTION

The present invention seeks to provide an improved suturing assembly, as described in more detail further below. The present invention is described for convenience with respect to the suturing device of PCT Patent Application WO 2009069119, but the invention is not limited to such a suturing device, and can be implemented in other suturing devices. The present invention is directed to a spacer that provides further functionality to suturing devices.

There is thus provided in accordance with an embodiment of the present invention a suturing assembly including a first puncture element including a sharp distal end for puncturing tissue, a second puncture element including a sharp distal end for puncturing tissue, the distal ends of the first and second puncture elements being spaced from each other by a gap, and a spacer arranged for sliding distally and proximally on at least one of the first and second puncture elements.

In accordance with an embodiment of the present invention the spacer is arranged to slide distally and proximally on both of the first and second puncture elements.

In accordance with an embodiment of the present invention the spacer is formed with a first opening through which one of the first and second puncture elements passes through, and a second opening through which the other of the first and second puncture elements passes through.

In accordance with an embodiment of the present invention the first opening has a closed outer contour.

In accordance with an embodiment of the present invention the second opening has a closed outer contour; alternatively, the outer contour of the second opening is not completely closed.

In accordance with an embodiment of the present invention the spacer includes a radially protruding flange.

In accordance with an embodiment of the present invention the spacer includes a distally protruding protector for protecting a distal tip of at least one of the first and second puncture elements.

In accordance with an embodiment of the present invention the spacer is arranged for pivoting about one of the first and second puncture elements and the spacer includes a connecting portion that snaps onto the other of the first and second puncture elements.

In accordance with an embodiment of the present invention, the suturing assembly further includes suture thread disposed along a portion of the first puncture element, wherein the suture thread is arranged to be grabbed at the distal end of the first puncture element, and a suture grabber positioned at the distal end of the second puncture element.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 3:
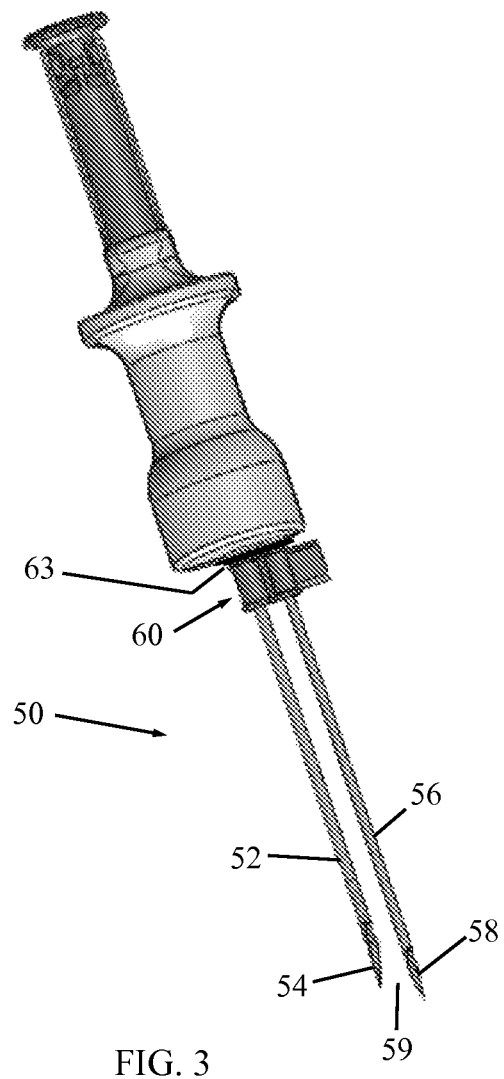
FIGS. 3 and 4 are simplified pictorial illustrations of a suturing assembly with a spacer, constructed and operative in accordance with an embodiment of the present invention, respectively with the spacer at proximal and distal ends of puncture elements.
Figure 4:
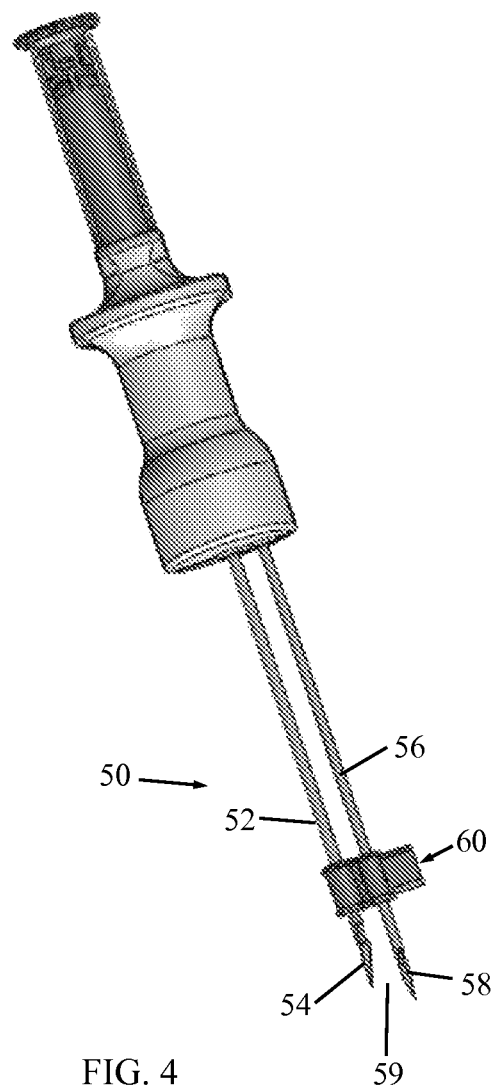
Figure 5:
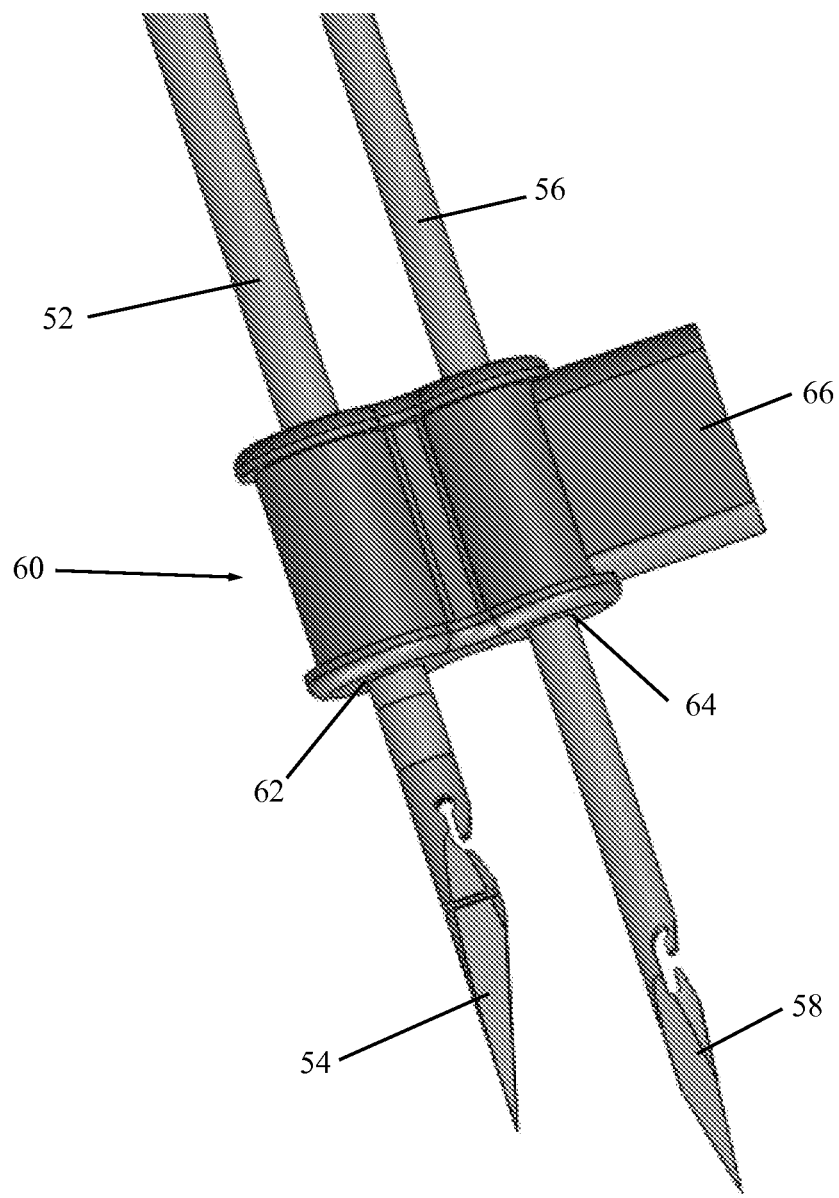
FIG. 5 is a more detailed illustration of the spacer of FIG. 4.

Reference is now made to FIGS. 3-5, which illustrate a suturing assembly 50, constructed and operative in accordance with a non-limiting embodiment of the present invention.

Suturing assembly 50 includes a first puncture element 52 including a sharp distal end 54 for puncturing tissue, and a second puncture element 56 including a sharp distal end 58 for puncturing tissue. The distal ends 54 and 58 of the first and second puncture elements 52 and 56 are spaced from each other by a gap 59. A spacer 60 is arranged for sliding distally and proximally on either one or both of first and second puncture elements 52 and 56. In the embodiment illustrated in FIG. 3, spacer 60 is arranged to slide distally and proximally on both of first and second puncture elements 52 and 56.

As seen best in FIG. 5, in accordance with an embodiment of the present invention, spacer 60 is formed with a first opening 62 through which one of the first and second puncture elements passes through, and a second opening 64 through which the other of the first and second puncture elements passes through. In the embodiments illustrated in FIGS. 5 and 6, each of the first and second openings 62 and 64 has a closed outer contour. In the embodiment illustrated in FIGS. 7 and 8, the outer contour of second opening 64 is not completely closed.

Spacer 60 is normally in the distal position (FIG. 4) prior to insertion of the first and second puncture elements 52 and 56 into tissue. The spacer 60 slides to the proximal position (FIG. 3) after insertion into the tissue. Optionally, as seen in FIG. 3, a biasing device 63, such as a coil spring, may be provided for urging spacer 60 from the proximal position to the distal position.

In accordance with an embodiment of the present invention the spacer includes a radially protruding flange 66, which may serve as a guide, handle or imaging landmark.

Figure 6:
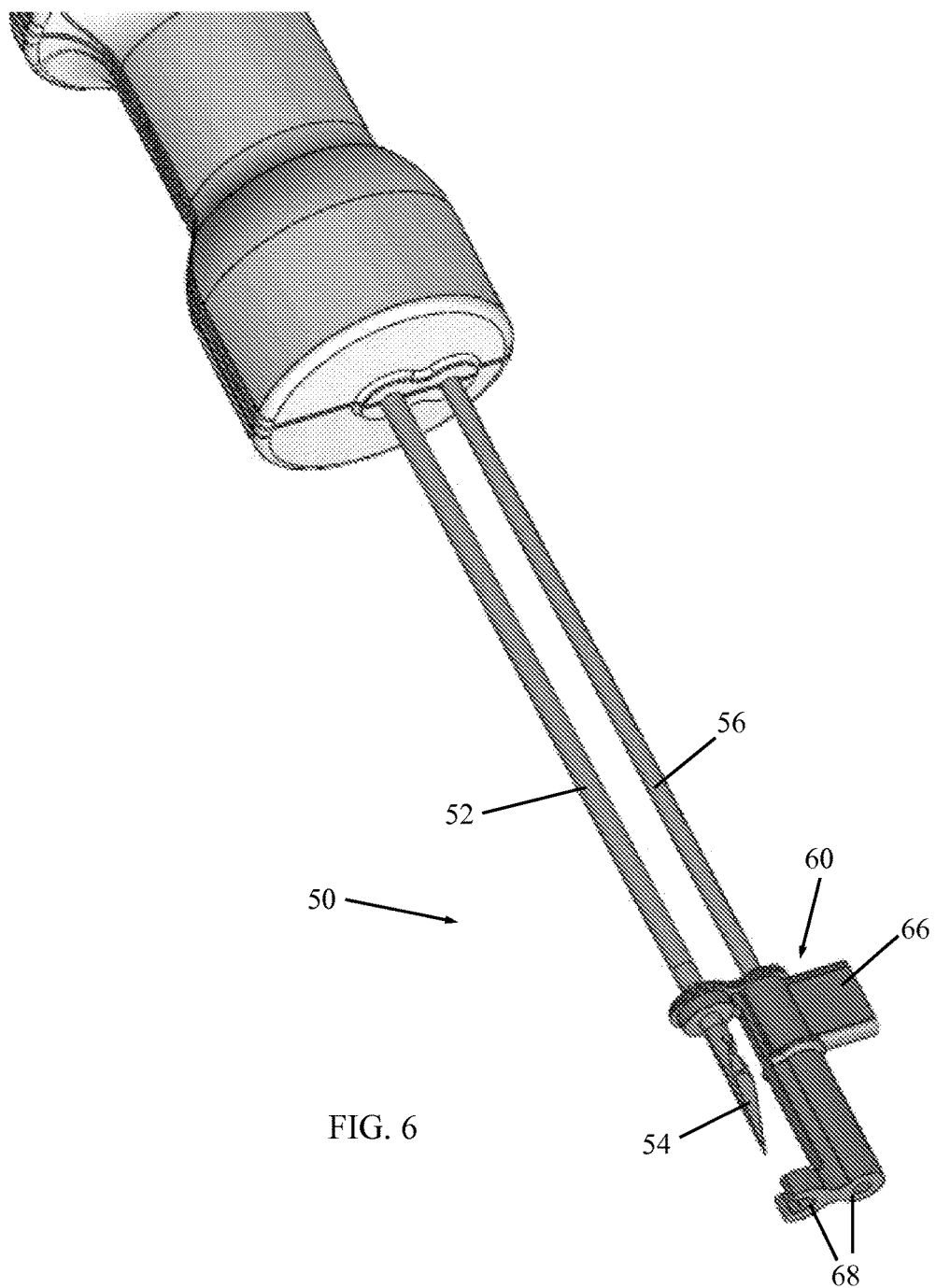
FIG. 6 is a simplified pictorial illustration of the spacer with a distally protruding protector, constructed and operative in accordance with an embodiment of the present invention.

Reference is now made to FIG. 6. In accordance with an embodiment of the present invention, spacer 60 includes one or more distally protruding protectors 68 for protecting one or both of distal ends 54 and 58 of the first and second puncture elements 52 and 56.

Figure 7:
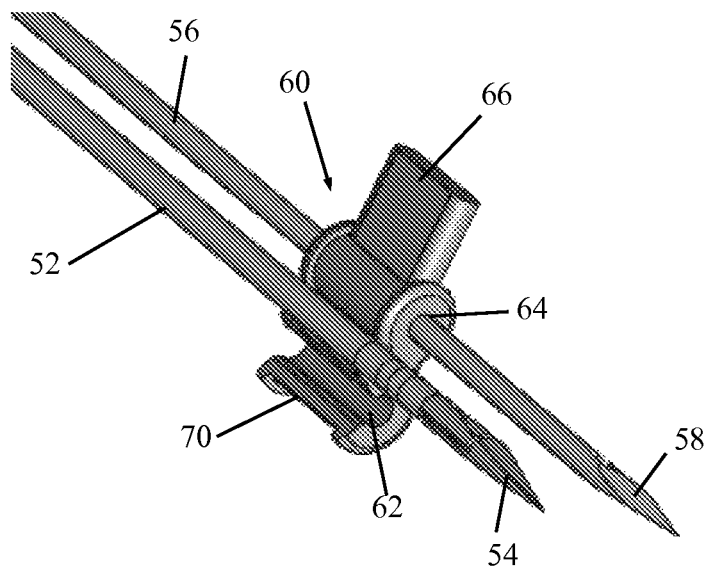
FIGS. 7 and 8 are simplified pictorial illustrations of the spacer, constructed and operative in accordance with an embodiment of the present invention, respectively before and after pivoting to snap onto one of the puncture elements.
Figure 8:
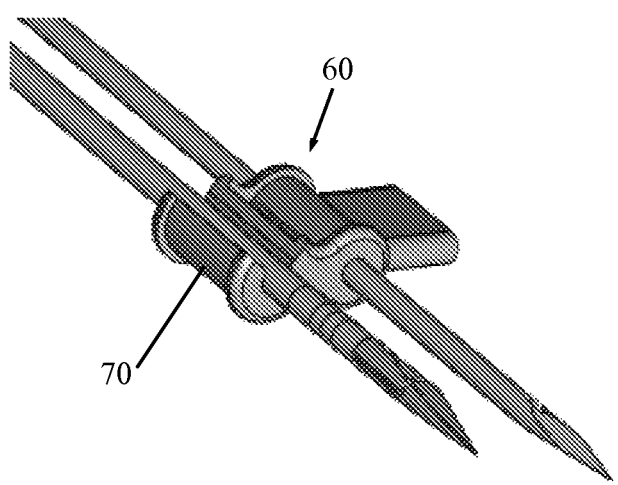

Reference is now made to FIGS. 7 and 8. In accordance with an embodiment of the present invention, spacer 60 is arranged for pivoting about one of the first and second puncture elements 52 or 56. Spacer 60 includes a connecting portion 70 that snaps onto the other of the first and second puncture elements.

Figure 1:
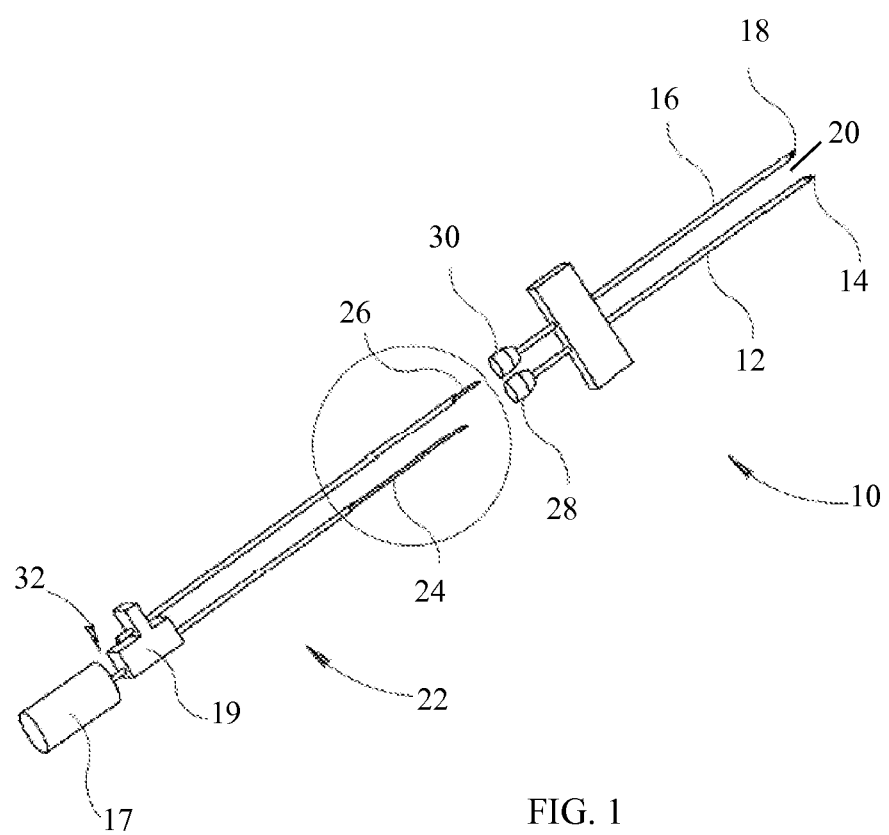
FIGS. 1 and 2 are simplified pictorial illustrations of a prior art suturing assembly, made according to PCT Patent Application WO 2009069119.
Figure 2:
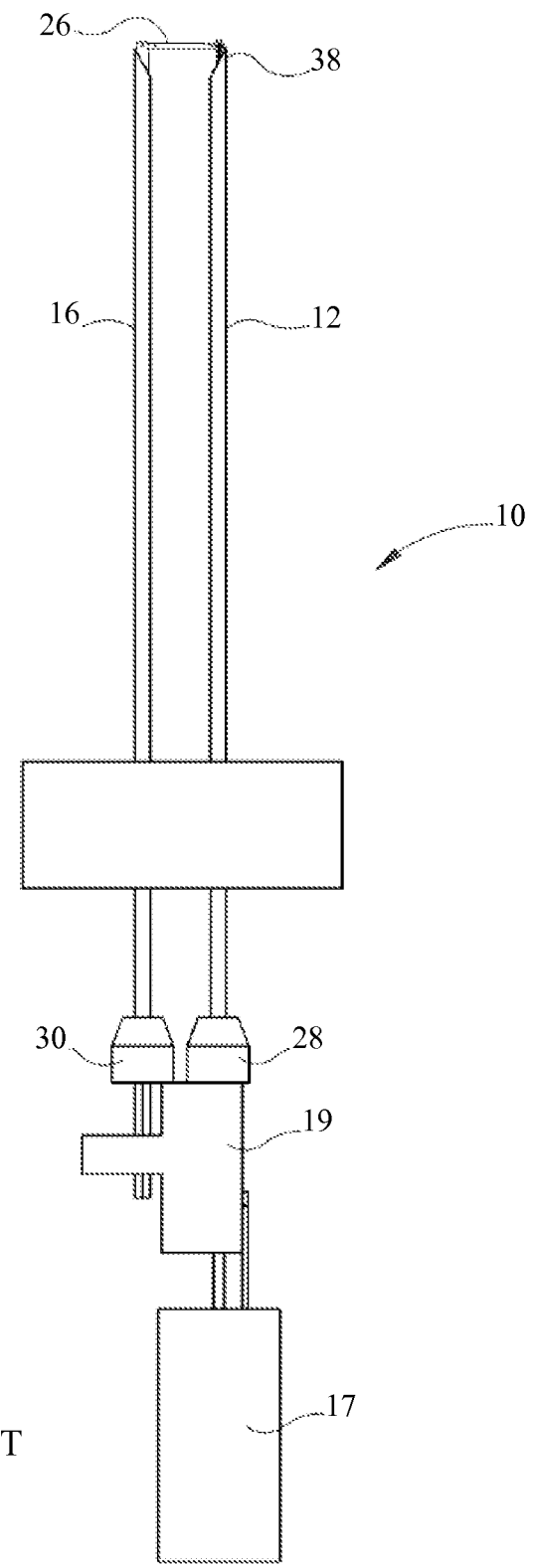

In accordance with an embodiment of the present invention, the suturing assembly may combine features of the prior art suturing device. For example, as shown previously in FIGS. 1 and 2, the suturing assembly may further include suture thread 38 disposed along a portion of the first puncture element 52, wherein the suture thread is arranged to be grabbed at the distal end of the first puncture element 52, and a suture grabber 26 positioned at the distal end of the second puncture element 54.

What is claimed is:

1. A suturing assembly comprising:
   a first puncture element comprising a sharp distal end for puncturing tissue;
   a second puncture element comprising a sharp distal end for puncturing tissue, the distal ends of said first and second puncture elements being spaced from each other by a gap; and
   a spacer arranged for sliding distally and proximally on at least one of said first and second puncture elements,
   wherein said spacer comprises a first interface portion formed with a first opening through which said first puncture element passes through, and a second interface portion formed with a second opening through which said second puncture element passes through, and a distally protruding protector that extends distally from said second interface portion, said distally protruding protector comprising a distal portion and an auxiliary portion that extends transversely from said distal portion and which is parallel to and spaced axially from said first interface portion, said distally protruding protector having an orientation in which said distal portion overlies a distal tip of said second puncture element but said auxiliary portion is spaced distally and axially from a distal tip of said first puncture element, and wherein said spacer comprises a flange that protrudes from a proximal portion of said second interface portion in a direction opposite to said first interface portion such that said second interface portion is between said first interface portion and said flange.

2. The suturing assembly according to claim 1, wherein said spacer is arranged to slide distally and proximally on both of said first and second puncture elements.

3. The suturing assembly according to claim 1, wherein said first opening has a closed outer contour.

4. The suturing assembly according to claim 1, wherein said second opening has a closed outer contour.

5. The suturing assembly according to claim 1, wherein an outer contour of said second opening is not completely closed.

6. The suturing assembly according to claim 1, wherein said auxiliary portion comprises a partial ring.

7. The suturing assembly according to claim 1, further comprising a biasing device for urging said spacer from a proximal position to a distal position.

8. The suturing assembly according to claim 1, further comprising suture thread disposed along a portion of said first puncture element, wherein said suture thread is arranged to be grabbed at the distal end of said first puncture element, and a suture grabber positioned at the distal end of said second puncture element.

9. A suturing assembly comprising:
   a first puncture element comprising a sharp distal end for puncturing tissue;
   a second puncture element comprising a sharp distal end for puncturing tissue, the distal ends of said first and second puncture elements being spaced from each other be a gap; and
   a spacer arranged for sliding distally and proximally on at least one of said first and second puncture elements,
   wherein said spacer comprises a first interface portion formed with a first opening through which said first puncture element passes through, and a second interface portion formed with a second opening through which said second puncture element passes through, and a distally protruding protector that extends distally from said second interface portion, said distally protruding protector comprising a distal portion and an auxiliary portion that extends transversely from said distal portion and which is parallel to and spaced axially from said first interface portion, said distally protruding protector having an orientation in which said distal portion overlies a distal tip of said second puncture element but said auxiliary portion is spaced distally and axially from a distal tip of said first puncture element, and wherein said distal portion covers a complete circumference of said second puncture element.

\* \* \* \* \*